United States Patent [19]

Sasaki et al.

[11] Patent Number: 4,470,841
[45] Date of Patent: Sep. 11, 1984

[54] CERTAIN HERBICIDAL PHOSPHONATES

[75] Inventors: Mitsuru Sasaki, Toyonaka; Ryo Yoshida, Kawanishi, both of Japan

[73] Assignee: Sumitomo Chemical Company, Limited, Osaka, Japan

[21] Appl. No.: 408,782

[22] Filed: Aug. 17, 1982

[30] Foreign Application Priority Data

Aug. 21, 1981 [JP] Japan ............................... 56-131694

[51] Int. Cl.$^3$ ........................... C07F 9/58; C07F 9/40; A01N 43/40; A01N 57/06
[52] U.S. Cl. ........................................ 71/86; 71/94; 260/951; 546/24
[58] Field of Search .......................... 260/951; 546/24; 424/200, 212; 71/94

[56] References Cited

U.S. PATENT DOCUMENTS 3,372,210 3/1968 Gutman et al. ..................... 260/951
3,954,442 5/1976 Becker et al. ......................... 71/108

FOREIGN PATENT DOCUMENTS 1519334 7/1978 United Kingdom .................. 71/108
1599121 9/1981 United Kingdom .................... 71/94

*Primary Examiner*—Alan L. Rotman
*Attorney, Agent, or Firm*—Birch, Stewart, Kolasch & Birch

[57] ABSTRACT

A herbicidal composition comprising as an active ingredient a compound of the formula:

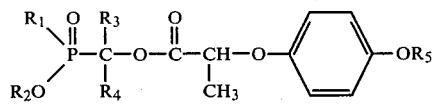

wherein $R_1$ is a $C_1$–$C_4$ alkyl group, a phenyl group or a $C_1$–$C_4$ alkoxy group, $R_2$ is a $C_1$–$C_4$ alkyl group, $R_3$ and $R_4$, which are the same or different, are each a hydrogen atom, a $C_1$–$C_4$ alkyl group or a phenyl group and $R_5$ is a 2,4-dichlorophenyl group, a 4-trifluoromethylphenyl group or a 5-trifluoromethylpyridin-2-yl group, and an inert carrier.

20 Claims, No Drawings

CERTAIN HERBICIDAL PHOSPHONATES

The present invention relates to organic phosphorous compounds, and their production and use. More particularly, it relates to organic phosphorus compounds of the formula:

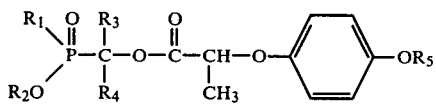

wherein $R_1$ is a $C_1$–$C_4$ alkyl group, a phenyl group or a $C_1$–$C_4$ alkoxy group, $R_2$ is a $C_1$–$C_4$ alkyl group, $R_3$ and $R_4$, which are the same or different, are each a hydrogen atom, a $C_1$–$C_4$ alkyl group or a phenyl group and $R_5$ is a 2,4-dichlorophenyl group, a 4-trifluoromethylphenyl group or a 5-trifluoromethylpyridin-2-yl group, and their production and use a herbicides.

Among the organic phosphorus compounds (I), preferred are those wherein $R_1$ is a $C_1$–$C_2$ alkyl group, a phenyl group or a $C_1$–$C_4$ alkoxy group, $R_2$ is a $C_1$–$C_4$ alkyl group, $R_3$ is a hydrogen atom, a $C_1$–$C_3$ alkyl group or a phenyl group, $R_4$ is a hydrogen atom or a methyl group and $R_5$ is a 2,4-dichlorophenyl group, a 4-trifluoromethylphenyl group or a 5-trifluoromethylpyridin-2-yl group.

It is known that certain kinds of 2-(substituted pheoxy)propionic acid derivatives, for instance, diclofop-methyl (i.e. methyl 2-[4-(2,4-dichlorophenoxy)phenoxy]propionate), metriflufen-methyl (i.e. methyl 2-[4-(4-trifluoromethylphenoxy)phenoxy]propionate) and fluazifop-butyl (i.e. butyl 2-[4-(5-trifluoromethyl-2-pyridyloxy)phenoxy]propionate), show a herbicidal activity against Graminaceous weeds (cf. U.S. Pat. No. 3,954,442, GB No. 1519334B, GB No. 2015995A, etc.). However, these known compounds have a poor selectivity between said harmful weeds and the important useful plants such as rice plant.

As a result of the extensive study, it has now been found that the organic phosphorus compounds (I) of the invention exhibit a prominent herbicidal potency against Graminaceous weeds germinated in the paddy field, particularly barnyard grass (*Echinochloa crusgalli*), while exerting no material phytotoxicity to the transplanted paddy rice. It has also been found that the organic phosphorus compounds (I) of the invention show an excellent herbicidal activity against the Graminaceous weeds in the crop field by pre-emergence soil treatment as well as post-emergence foliar treatment. Particularly, in the post-emergence treatment, they show a strong herbicidal activity against a variety of Graminaceous weeds such as wild oat (*Avena fatua*), barnyard grass, green foxtail (*Setaria viridis*), blackgrass (*Alopecurus myosuroides*), downy brome (*Bromus tectorum*), johnsongrass (*Sorghum halepense*), large crabgrass (Digitaria sanguinalis), annual bluegrass (*Poa annua*), volunteer corn (Zea mays), etc. without any material phytotoxicity to broad-leaved crop plants such as soybeans, cotton or sugarbeet, etc. Besides, they can be safely applied to the wheat fields to exterminate or prevent wild oat, barnyard grass, green foxtail, blackgrass, downy brome, etc. germinated therein. Thus, the organic phosphorus compounds (I) can be used as herbicides applicable for the fields of crops and vegetables, etc.

The organic phosphorus compound (I) can be produced by reacting a hydroxyl compound of the formula:

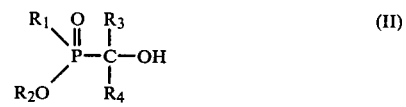

wherein $R_1$, $R_2$, $R_3$ and $R_4$ are each as defined above with an acid halide of the formula:

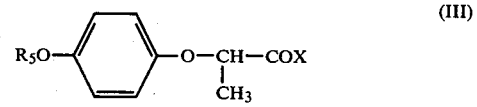

wherein X is a halogen atom (e.g. chlorine, bromine) and $R_5$ is as defined above in an inert solvent (e.g. water, chloroform, ether, benzene, toluene) in the presence of a base such as an organic tertiary amine (e.g. pyridine, triethylamine, N,N-dimethylaniline) or an inorganic base (e.g. sodium hydroxide, potassium hydroxide, sodium carbonate, potassium carbonate). The base may be employed in an amount of 1 to 2 equivalents to the hydroxyl compound (II).

The reaction proceeds ordinarily at a temperature of −70° C. to 50° C. and can be accomplished within a period of 10 minutes to 24 hours, although it varies depending upon the starting materials. By usual work-up, the objective organic phosphorus compound (I) is obtainable in a high yield. If necessary, however, purification such as column chromatography may be applied.

The hydroxyl compound (II) used as the starting material in the above reaction can be produced according to the method as described in Howben-Weyl: Methoden der Organischen Chemie, 12 (1), p. 475 (1964). Namely, it can be produced from the reaction between aldehydes (or ketones) and phosphonic acid or its ester.

Alternatively, the organic phosphorus compound (I) can be obtainable by reacting an acid ester of the formula:

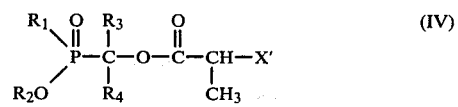

wherein X' is a halogen atom (e.g. chlorine, bromine) and $R_1$, $R_2$, $R_3$ and $R_4$ are each as defined above with a hydroxyphenyl ether of the formula:

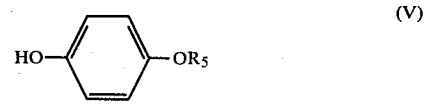

wherein $R_5$ is as defined above in an organic solvent such as ketones (e.g. acetone, methylisobutylketone), dimethylformamide or diethylformamide in the presence of a base (e.g. sodium carbonate, potassium carbonate). The base may be employed in an amount of 1 to 1.5 equivalents to the acid ester (IV).

The reaction proceeds ordinarily at a temperature of 50° C. to the refluxing temperature of the solvent and can be accomplished within a period of 3 to 12 hours, although it varies depending upon the starting materials. By usual work-up, the objective organic phosphorus compund (I) is obtainable in a high yield. If necessary, however, purification such as column chromatography may be applied.

Some embodiments of the procedures for production of the organic phosphorus compounds (I) are illustratively shown in the following Examples.

EXAMPLE 1

O,O-Diisopropyl hydroxymethyl phosphonate (1.0 g) and pyridine (1.0 g) were dissolved in chloroform (10 ml), and α-4-(2',4'-dichlorophenoxy)phenoxypropionyl chloride (1.7 g) was dropwise added thereto while stirring at 0° to 5° C. under ice-cooling. The resultant mixture was stirred at room temperature (ca. 20° C.) for 20 hours. A 3% aqueous solution of hydrochloric acid (30 ml) was added thereto. Thirty minutes thereafter, the reaction mixture was separated in a separatory funnel. The chloroform layer was washed with water, dried over magnesium sulfate and filtered. Chloroform was evaporated in vacuo, and the residue was purified by silica gel chromatography to give 1.26 g of O,O-diisopropylphosphonomethyl α-4-(2',4'-dichlorophenoxy)phenoxypropionate (Compound No. 3). $n_D^{21.5}$ 1.5212.

EXAMPLE 2

O,O-Diethyl hydroxymethyl phosphonate (0.5 g) and pyridine (0.5 g) were dissolved in chloroform (5 ml), and the resultant solution was cooled to −20° C. α-4-(4'-Trifluoromethylphenoxy)phenoxypropionyl chloride (1.1 g) was dropwise added thereto while stirring. After allowed to stand at room temperature for 2 hours and at 50° C. for 3 hours, the resulting mixture was cooled, and a 3% aqueous solution of hydrochloric acid (20 ml) was added thereto. Thirty minutes thereafter, the reaction mixture was separated in a separatory funnel. The chloroform layer was washed with water, dried over anhydrous magnesium sulfate and filtered. Chloroform was evaporated in vacuo to give 1.03 g of O,O-diethylphosphonomethyl α-4-(4'-trifluoromethylphenoxy)phenoxypropionate (Compound No. 6). $n_D^{20}$ 1.5000.

EXAMPLE 3

O,O-Diethyl α-hydroxyethyl phosphonate (1.8 g) and triethylamine (2.0 g) were dissolved in ether (20 ml), and the resultant solution was cooled to 10° C. while stirring. α-4-(5'-Trifluoromethylpyridin-2-yloxy)phenoxypropionyl chloride (3.7 g) was added thereto at 10° to 20° C., and the resulting mixture was allowed to stand at a room temperature for 24 hours, followed by addition of water (20 ml). The reaction mixture was separated in a separatory funnel. The ether layer was dried over anhydrous magnesium sulfate and filtered. Ether was evaporated in vacuo, and the residue was purified by silica gel chromatography to give 3.5 g of α-(O,O-diethylphosphono)ethyl α'-4-(5'-trifluoromethylpyridin-2-yloxy)phenoxypropionate (Compound No. 11). $n_D^{24.0}$ 1.4780.

EXAMPLE 4

α-(O,O-Diethylphosphono)benzyl α'-bromopropionate (3.8 g) and 4-(5'-trifluoromethylpyridin-2-yloxy)phenol (2.6 g) were dissolved in dimethylformamide (30 ml). Potassium carbonate (1.5 g) was added thereto. The resultant mixture was allowed to stand at 90° to 100° C. for 2 hours and cooled. The reaction mixture was poured onto ice-water (50 g) and extracted with ether (20 ml×3 times). The ether layer was washed with water, dried over anhydrous magnesium sulfate and filtered. Ether was evaporated in vacuo to give 3.6 g of α-(O,O-diethylphosphono)benzyl α'-4-(5'-trifluoromethylpyridin-2-yloxy)phenoxypropionate (Compound No. 19). $n_D^{26.0}$ 1.5118).

Examples of the organic phosphorus compounds (I) produced by the same manner as above are shown in Table 1.

TABLE 1

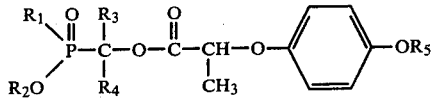

| Compound No. | $R_1$ | $R_2$ | $R_3$ | $R_4$ | $R_5$ | Physical property |
|---|---|---|---|---|---|---|
| 1 | CH$_3$O | CH$_3$ | H | H | 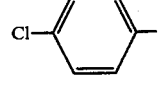 | $n_D^{24.0}$ 1.5466 |
| 2 | C$_2$H$_5$O | C$_2$H$_5$ | H | H | | $n_D^{24.0}$ 1.5380 |
| 3 | (i)C$_3$H$_7$O | (i)C$_3$H$_7$ | H | H | 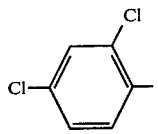 | $n_D^{21.5}$ 1.5212 |

TABLE 1-continued $$\underset{R_2O}{\overset{R_1}{\underset{}{\vphantom{|}}}}\overset{O}{\underset{}{\vphantom{|}}}P-\underset{R_4}{\overset{R_3}{\underset{}{\vphantom{|}}}}C-O-\overset{O}{\underset{}{\vphantom{|}}}C-CH-O-\bigcirc-OR_5$$
(with CH₃ on the CH)

| Compound No. | R₁ | R₂ | R₃ | R₄ | R₅ | Physical property |
|---|---|---|---|---|---|---|
| 4 | (n)C₃H₇O | (n)C₃H₇ | H | H | 2,4-dichlorophenyl | $n_D^{22.0}$ 1.5468 |
| 5 | (n)C₄H₉O | (n)C₄H₉ | H | H | 2,4-dichlorophenyl | $n_D^{22.0}$ 1.5470 |
| 6 | C₂H₅O | C₂H₅ | H | H | 4-(F₃C)phenyl | $n_D^{20.0}$ 1.5000 |
| 7 | (i)C₃H₇O | (i)C₃H₇ | CH₃ | H | 4-(F₃C)phenyl | $n_D^{24.0}$ 1.4830 |
| 8 | CH₃O | CH₃ | CH₃ | H | 4-(F₃C)phenyl | $n_D^{24.0}$ 1.4991 |
| 9 | C₂H₅O | C₂H₅ | CH₃ | H | 4-(F₃C)phenyl | $n_D^{24.0}$ 1.4873 |
| 10 | (n)C₄H₉O | (n)C₄H₉ | CH₃ | H | 4-(F₃C)phenyl | $n_D^{24.5}$ 1.4850 |
| 11 | C₂H₅O | C₂H₅ | CH₃ | H | 5-(F₃C)-2-pyridyl | $n_D^{24.0}$ 1.4780 |
| 12 | (i)C₃H₇O | (i)C₃H₇ | H | H | 5-(F₃C)-2-pyridyl | $n_D^{24.5}$ 1.4958 |
| 13 | (i)C₃H₇O | (i)C₃H₇ | CH₃ | H | 5-(F₃C)-2-pyridyl | $n_D^{24.5}$ 1.4770 |
| 14 | (n)C₄H₉O | (n)C₄H₉ | CH₃ | H | 5-(F₃C)-2-pyridyl | $n_D^{24.5}$ 1.4740 |

TABLE 1-continued $$\underset{R_2O}{\overset{R_1}{\diagdown}}\overset{O}{\underset{\|}{P}}-\overset{R_3}{\underset{R_4}{C}}-O-\overset{O}{\underset{\|}{C}}-\underset{CH_3}{CH}-O-\underset{}{\underset{}{\bigcirc}}-OR_5$$

| Compound No. | $R_1$ | $R_2$ | $R_3$ | $R_4$ | $R_5$ | Physical property |
|---|---|---|---|---|---|---|
| 15 | $CH_3O$ | $CH_3$ | $CH_3$ | H | 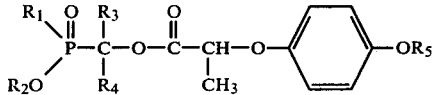 | $n_D^{23.5}$ 1.4920 |
| 16 | $CH_3O$ | $CH_3$ | 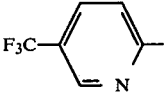 | H | 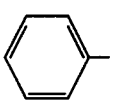 | $n_D^{23.5}$ 1.5273 |
| 17 | $C_2H_5O$ | $C_2H_5$ | H | H | 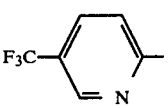 | $n_D^{22.5}$ 1.4962 |
| 18 | $CH_3O$ | $CH_3$ | $CH_3$ | $CH_3$ | 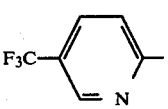 | $n_D^{26.0}$ 1.5092 |
| 19 | $C_2H_5O$ | $C_2H_5$ | 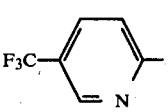 | H | 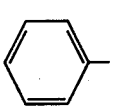 | $n_D^{26.0}$ 1.5118 |
| 20 | $CH_3$ | $C_2H_5$ | H | H | 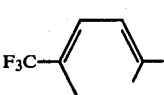 | $n_D^{24.0}$ 1.4790 |
| 21 | 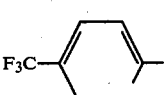 | $C_2H_5$ | H | H | 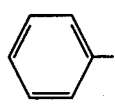 | $n_D^{24.0}$ 1.5120 |
| 22 | $C_2H_5$ | $C_2H_5$ | H | H | 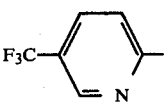 | $n_D^{25.0}$ 1.4920 |
| 23 | $C_2H_5O$ | $C_2H_5$ | $C_2H_5$ | H | 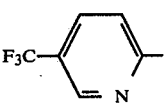 | $n_D^{25.0}$ 1.4820 |
| 24 | $C_2H_5O$ | $C_2H_5$ | (i)$C_3H_7$ | H | 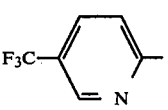 | $n_D^{25.0}$ 1.4835 |

In the practical usage of the organic phosphorus compounds (I), they may be applied as such or in any composition form such as wettable powders, emulsifiable concentrates, granules, fine granules or dusts.

For formulation of those compositions, a solid or liquid carrier or diluent may be used. As for the solid carrier or diluent, there may be exemplified mineral powders (e.g. kaolin, bentonite, montmorillonite, talc, diatomaceous earth, mica, vermiculite, gypsum, calcium carbonate, apatite, synthetic hydrated silica), vegetable powders (e.g. soybean powder, wheat flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, isophorone, cyclohexanone), esters (ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethyleneoxypropylene polymers, polyoxyethylene alkyl phosphates, fatty acid salts, alkyl sulfates, alkyl sulfonates, alkylaryl sulfonates, alkyl phosphates, polyoxyethylene alkyl sulfate, quaternary ammonium salts, and the like. But the surface active agent is not of course limited to these compounds. And, if necessary, gelatin, casein, sodium alginte, starch, agar, polyvinyl alcohol, ligninsulfonic acid, isopropyl acid phosphate, alginates or the like may be used as auxiliary agents.

The organic phosphorus compounds (I) of the invention may be used together with other herbicides to improve their activity as herbicides, and in some cases, a synergistic effect can be expected. As the herbicides to be mixed with, there may be given 2,4-dichlorophenoxyacetic acid, sodium 5-[2-chloro-4-(trifluoromethyl)-phenoxy]-2-nitrobenzoate, 2-chloro-4-ethylamino-6-isopropylamino-s-triazine, 2-methylthio-4,6-bis(isopropylamino)-s-triazine, 3-(3,4-dichlorophenyl)-1,1-dimethylurea, 3-[4-(4-chlorophenoxy)phenyl]-1,1-dimethylurea, 3-($\alpha,\alpha,\alpha$-trifluoro-m-tolyl)-1,1-dimethylurea, isopropyl N-(3-chlorophenyl)-carbamate, 3,4-dichloropropionanilide, 3-cyclohexyl-5,6-trimethyleneuracil, O-ethyl O-(5-methyl-2-nitrophenyl)-N-sec-butylphosphoramidothioate, 3-isopropyl-1H-2,1,3-benzothiadiazin-(4)-3H-one-2,2-dioxide, disodium methanearsonate, etc.

In the herbicidal composition of the invention, the content of the organic phosphorus compounds (I) may be from 0.5 to 90% by weight, preferably from 1 to 80% by weight.

Practical embodiments of the herbicidal composition according to the invention are illustratively shown in the following examples wherein parts and % are by weight. The compound number of the active ingredient corresponds to the one in Table 1.

FORMULATION EXAMPLE 1

Forty parts of Compound No. 3, 2 parts of polyoxyethylene alkylaryl ether, 30 parts of synthetic hydrated silica and 28 parts of diatomaceous earth are well mixed while being powdered to obtain a wettable powder.

FORMULATION EXAMPLE 2

Ten parts of Compound No. 6, 7 parts of polyoxyethylene alkylaryl ether, 3 parts of alkylarylsulfonate and 80 parts of xylene are well mixed while being powdered to obtain an emulsifiable concentrate.

FORMULATION EXAMPLE 3

One part of Compound No. 9, 1 part of synthetic hydrated silica, 5 parts of lignin sulfonate and 93 parts of kaolin are well mixed while being powdered. The mixture is then kneaded with water, granulated and dried to obtain granules.

FORMULATION EXAMPLE 4

Forty parts of bentonite, 5 parts of lignin sulfonate and 55 parts of kaolin are well mixed while being powdered. The mixture is then kneaded with water, granulated and dried to obtain granules containing no active ingredient. Five parts of Compound No. 17 are immersed therein to obtain a granule.

FORMULATION EXAMPLE 5

Three parts of Compound No. 19, 0.5 part of isopropyl acid phosphate, 66.5 parts of kaolin and 30 parts of talc are well mixed while being powdered to obtain a dust.

FORMULATION EXAMPLE 6

Twenty parts of Compound No. 3 is mixed with 60 parts of an aqueous solution containing 3% polyoxyethylene sorbitan monolactate and grained until the particle size of the active ingredient becomes less than 3 microns. Twenty parts of an aqueous solution containing 3% of sodium alginate as a dispersing agent is incorporated therein to obtain a suspension.

The dosage rate of the organic phosphorus compounds (I) may vary on the kind of preparation, sorts of weeds or crop plants, the weather condition, etc. Generally, however, the dosage rate may be from 0.5 to 100 grams, preferably from 1 to 50 grams, of the active ingredient per are.

The application of the organic phosphorus compounds (I) as herbicides will be illustratively shown in the following Examples wherein the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the phytotoxicity to crop plants and the herbicidal activity on weeds were evaluated by the standard given in the table below. The rating values of phytotoxicity, 0 and 1, and those of herbicidal activity, 5 and 4, are generally regarded as satisfactory to protect crop plants and control weeds, respectively. The rating values in the paddy field test alone were calculated from the dry weight of the test plants.

| Rating value | Fresh weight (percentage to untreated plot) (%) | |
|---|---|---|
| | Phytotoxicity to crop plants | Herbicidal activity on weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

TEST EXAMPLE 1

Wagner's pots (1/5000 are) were filled with paddy field soil containing the seeds of barnyard grass and broad-leaved weeds (e.g. monochoria, false pimpernel, toothcup) and flooded with water to make a paddy field condition. Rice seedlings of the 3-leaf stage was transplanted therein and grown for 7 days. A designed amount of the test compound formulated in a wettable powder according to Formulation Example 1 and diluted with water was applied to the pots where the rice plants were grown up to the 4.3 leaf stage and the barnyard grass up to the 0.5–1 leaf stage. After 20 days, herbicidal activity and phytotoxicity were examined. The results are shown in Table 2.

TABLE 2

| Compound No. | Dosage (weight of active ingredient, g/are) | Phytotoxicity Rice plant | Herbicidal activity Barnyardgrass | Herbicidal activity Broad-leaved weed |
|---|---|---|---|---|
| 1 | 20 | 1 | 5 | 3 |
|   | 10 | 0 | 5 | 3 |
|   | 5 | 0 | 4 | 2 |
| 2 | 20 | 1 | 5 | 3 |
|   | 10 | 0 | 5 | 2 |
|   | 5 | 0 | 5 | 1 |
| 3 | 20 | 1 | 5 | 4 |
|   | 10 | 1 | 5 | 4 |
|   | 5 | 0 | 5 | 3 |
| 4 | 20 | 0 | 5 | 2 |
|   | 10 | 0 | 5 | 1 |
|   | 5 | 0 | 4 | 1 |
| 5 | 20 | 0 | 5 | 2 |
|   | 10 | 0 | 5 | 1 |
|   | 5 | 0 | 4 | 0 |
| 6 | 10 | 1 | 5 | 4 |
|   | 5 | 0 | 5 | 3 |
|   | 2.5 | 0 | 5 | 2 |
| Diclofop-methyl | 20 | 4 | 5 | 3 |
|   | 10 | 3 | 5 | 2 |
|   | 5 | 1 | 3 | 1 |
| Metriflufen-methyl | 10 | 5 | 5 | 2 |
|   | 5 | 5 | 5 | 1 |
|   | 2.5 | 3 | 4 | 1 |

TEST EXAMPLE 2

Wagner's pots (1/5000 are) were filled with paddy field soil containing the seeds of barnyardgrass and flooded with water to make a paddy field condition. Rice seedlings of the 3-leaf stage was transplanted therein and grown for 12 days in a greenhouse, whereby the rice seedlings grown up to the two-tillers stage and the barnyardgrass to the 2-leaf stage. A designed amount of the test compound formulated in an emulsifiable concentrate according to Formulation Example 2 and diluted with 5 ml of water was applied to the pots. After 20 days, herbicidal activity and phytotoxicity were examined. The results are shown in Table 3.

TABLE 3

| Compound No. | Dosage (weight of active ingredient, g/are) | Phytotoxicity Rice plant | Herbicidal activity Barnyardgrass |
|---|---|---|---|
| 7 | 5 | 1 | 5 |
|   | 2.5 | 0 | 5 |
|   | 1.25 | 0 | 5 |
| 9 | 5 | 0 | 5 |
|   | 2.5 | 0 | 5 |
|   | 1.25 | 0 | 5 |
| 11 | 5 | 1 | 5 |
|   | 2.5 | 0 | 5 |
|   | 1.25 | 0 | 4 |
| 12 | 5 | 2 | 5 |
|   | 2.5 | 1 | 5 |
|   | 1.25 | 0 | 5 |
| 13 | 5 | 2 | 5 |
|   | 2.5 | 1 | 5 |
|   | 1.25 | 0 | 5 |
| 14 | 5 | 2 | 5 |
|   | 2.5 | 0 | 5 |
|   | 1.25 | 0 | 5 |
| 16 | 5 | 1 | 5 |
|   | 2.5 | 1 | 5 |
|   | 1.25 | 0 | 4 |
| 17 | 5 | 2 | 5 |
|   | 2.5 | 0 | 5 |
|   | 1.25 | 0 | 4 |
| 19 | 5 | 2 | 5 |
|   | 2.5 | 1 | 5 |
|   | 1.25 | 0 | 4 |
| 20 | 5 | 1 | 5 |
|   | 2.5 | 1 | 5 |
|   | 1.25 | 0 | 5 |
| 21 | 5 | 1 | 5 |
|   | 2.5 | 0 | 5 |
|   | 1.25 | 0 | 5 |
| Fluazifop-butyl | 5 | 5 | 5 |
|   | 2.5 | 4 | 5 |
|   | 1.25 | 2 | 4 |
| Metriflufen-methyl | 5 | 5 | 5 |
|   | 2.5 | 3 | 4 |
|   | 1.25 | 2 | 3 |

TEST EXAMPLE 3

Plastic trays (35 cm × 25 cm × 15 cm) were filled with upland field soil, and the seeds of wheat and sugarbeet and the seeds of wild oat, barnyard grass, green foxtail, blackgrass and downy brome were sowed therein and grown for 3 weeks in a greenhouse. Each two rays were placed into a flame of 50 cm × 100 cm × 40 cm and a designed amount of the test compound formulated into an emulsifiable concentrate according to Formulation Example 2 and dispersed in water with a wetting agent was sprayed over the top by means of a small hand sprayer to the foliage of the test plants at a spray volume of 5 liters per are. After the spraying, the test plants were grown in the greenhouse for 3 weeks, and phytotoxicity and herbicidal activity were examined. The results are shown in Table 4. At the time of the treatment, the test plants were in a 2 to 4-leaf stage and in 5 to 15 cm heights, although they varied depending on their kinds.

TABLE 4

| Compound No. | Dosage (weight of active ingredient g/are) | Phytotoxicity Wheat | Phytotoxicity Sugarbeet | Herbicidal activity Wild oat | Herbicidal activity Barnyardgrass | Herbicidal activity Green foxtail | Herbicidal activity Blackgrass | Herbicidal activity Downy brome |
|---|---|---|---|---|---|---|---|---|
| 1 | 20 | 0 | 0 | 5 | 5 | 5 | 5 | 2 |
|   | 10 | 0 | 0 | 5 | 5 | 5 | 4 | 2 |
|   | 5 | 0 | 0 | 3 | 5 | 5 | 3 | 0 |
| 2 | 20 | 1 | 0 | 5 | 5 | 5 | 5 | 3 |
|   | 10 | 1 | 0 | 5 | 5 | 5 | 5 | 3 |
|   | 5 | 0 | 0 | 5 | 5 | 5 | 3 | 2 |

TABLE 4-continued

| Compound No. | Dosage (weight of active ingredient g/are) | Phytotoxicity Wheat | Phytotoxicity Sugar-beet | Wild oat | Barnyard-grass | Green foxtail | Black-grass | Downy brome |
|---|---|---|---|---|---|---|---|---|
| 3 | 20 | 2 | 0 | 5 | 5 | 5 | 5 | 4 |
|  | 10 | 1 | 0 | 5 | 5 | 5 | 5 | 3 |
|  | 5 | 0 | 0 | 5 | 5 | 5 | 5 | 2 |
| 4 | 20 | 1 | 5 | 5 | 5 | 5 | 5 | 3 |
|  | 10 | 0 | 0 | 5 | 5 | 5 | 4 | 2 |
|  | 5 | 0 | 0 | 4 | 5 | 5 | 3 | 1 |
| 5 | 20 | 1 | 0 | 5 | 5 | 5 | 5 | 3 |
|  | 10 | 0 | 0 | 5 | 5 | 5 | 5 | 3 |
|  | 5 | 0 | 0 | 5 | 5 | 5 | 3 | 1 |
| 6 | 10 | 5 | 1 | 5 | 5 | 5 | 5 | 5 |
|  | 2.5 | 5 | 0 | 5 | 5 | 5 | 5 | 5 |
| 8 | 10 | 5 | 0 | 5 | 5 | 5 | 5 | 5 |
|  | 2.5 | 5 | 0 | 5 | 5 | 5 | 5 | 5 |
| 9 | 10 | 5 | 0 | 5 | 5 | 5 | 5 | 5 |
|  | 2.5 | 5 | 0 | 5 | 5 | 5 | 5 | 5 |
| 10 | 10 | 5 | 1 | 5 | 5 | 5 | 5 | 5 |
|  | 2.5 | 5 | 0 | 5 | 5 | 5 | 5 | 5 |
| 11 | 10 | 5 | 0 | 5 | 5 | 5 | 5 | 5 |
|  | 2.5 | 5 | 0 | 5 | 5 | 4 | 5 | 5 |
| 12 | 10 | 5 | 0 | 5 | 5 | 5 | 5 | 5 |
|  | 2.5 | 5 | 0 | 5 | 5 | 5 | 5 | 5 |
| 15 | 10 | 5 | 1 | 5 | 5 | 5 | 5 | 5 |
|  | 2.5 | 5 | 0 | 5 | 5 | 5 | 5 | 4 |
| 18 | 10 | 5 | 0 | 5 | 5 | 5 | 5 | 5 |
|  | 2.5 | 5 | 0 | 5 | 5 | 3 | 5 | 4 |
| 21 | 10 | 5 | 1 | 5 | 5 | 5 | 5 | 5 |
|  | 2.5 | 5 | 0 | 5 | 5 | 5 | 5 | 5 |
| 22 | 10 | 5 | 0 | 5 | 5 | 5 | 5 | 5 |
|  | 2.5 | 5 | 0 | 5 | 5 | 5 | 5 | 5 |
| 23 | 10 | 5 | 0 | 5 | 5 | 5 | 5 | 5 |
|  | 2.5 | 5 | 0 | 5 | 5 | 5 | 5 | 5 |
| 24 | 10 | 5 | 1 | 5 | 5 | 5 | 5 | 5 |
|  | 2.5 | 5 | 0 | 5 | 5 | 4 | 5 | 5 |
| Diclofop-methyl | 40 | 4 | 1 | 5 | 5 | 5 | 5 | 3 |
|  | 20 | 2 | 0 | 5 | 5 | 5 | 4 | 2 |
|  | 10 | 2 | 0 | 4 | 5 | 5 | 4 | 2 |
|  | 5 | 1 | 0 | 3 | 5 | 5 | 2 | 1 |
| Metriflufen-methyl | 20 | 5 | 1 | 5 | 5 | 5 | 5 | 5 |
|  | 10 | 5 | 1 | 5 | 5 | 5 | 5 | 4 |
|  | 5 | 5 | 0 | 5 | 5 | 5 | 4 | 3 |
|  | 2.5 | 5 | 0 | 3 | 5 | 5 | 3 | 2 |
| Fluazifop-butyl | 10 | 5 | 1 | 5 | 5 | 5 | 5 | 5 |
|  | 2.5 | 5 | 0 | 5 | 5 | 4 | 5 | 3 |

TEST EXAMPLE 4

Plastic trays (35 cm×25 cm×15 cm) were filled with upland field soil, and the seeds of soybeans and cotton and the seeds of barnyard grass, volunteer corn, green foxtail, johnsongrass and large crabgrass were sowed therein and grown for 2 to 3 weeks in a greenhouse. Each two rays were placed into a flame of 50 cm×100 cm×90 cm and a designed amount of the test compound formulated into an emulsifiable concentrate according to Formulation Example 2 and dispersed in water with a wetting agent was sprayed over the top by means of a small hand sprayer to the foliage of the test plants at a spray volume of 5 liters per are. After the spraying, the test plants were grown in the greenhouse for 3 weeks, and phytotoxicity and herbicidal activity were examined. The results are shown in Table 5. At the time of the treatment, the test plants were in a 1 to 4-leaf stage and in 2 to 20 cm heights, although they varied depending on their kinds.

TABLE 5

| Compound No. | Dosage (weight of active ingredient, g/are) | Phytotoxicity Soybean | Phytotoxicity Cotton | Barnyard-grass | Volunteer corn | Green fox-tail | Johnson-grass | Large crab-grass |
|---|---|---|---|---|---|---|---|---|
| 1 | 20 | 0 | 0 | 5 | 5 | 5 | 2 | 5 |
|  | 5 | 0 | 0 | 5 | 3 | 5 | 0 | 3 |
| 2 | 20 | 0 | 0 | 5 | 5 | 5 | 3 | 5 |
|  | 5 | 0 | 0 | 5 | 5 | 5 | 2 | 4 |
| 3 | 20 | 0 | 0 | 5 | 5 | 5 | 4 | 5 |
|  | 5 | 0 | 0 | 5 | 5 | 5 | 3 | 4 |
| 4 | 20 | 0 | 0 | 5 | 5 | 5 | 4 | 5 |
|  | 5 | 0 | 0 | 5 | 5 | 5 | 3 | 3 |
| 5 | 20 | 0 | 0 | 5 | 5 | 5 | 4 | 5 |
|  | 5 | 0 | 0 | 5 | 5 | 5 | 3 | 5 |
| 6 | 10 | 0 | 0 | 5 | 5 | 5 | 5 | 5 |

TABLE 5-continued

| Compound No. | Dosage (weight of active ingredient, g/are) | Phytotoxicity Soybean | Phytotoxicity Cotton | Herbicidal activity Barnyard-grass | Volunteer corn | Green fox-tail | Johnson-grass | Large crab-grass |
|---|---|---|---|---|---|---|---|---|
| 8 | 2.5 | 0 | 0 | 5 | 5 | 5 | 5 | 5 |
|   | 10 | 0 | 0 | 5 | 5 | 5 | 5 | 5 |
| 9 | 2.5 | 0 | 0 | 5 | 5 | 5 | 5 | 5 |
|   | 10 | 1 | 0 | 5 | 5 | 5 | 5 | 5 |
| 10 | 2.5 | 0 | 0 | 5 | 5 | 5 | 5 | 5 |
|    | 10 | 1 | 0 | 5 | 5 | 5 | 5 | 5 |
| 11 | 2.5 | 0 | 0 | 5 | 5 | 5 | 5 | 5 |
|    | 10 | 0 | 0 | 5 | 5 | 4 | 5 | 5 |
| 12 | 2.5 | 0 | 0 | 5 | 5 | 5 | 5 | 5 |
|    | 10 | 0 | 0 | 5 | 5 | 5 | 5 | 5 |
| 15 | 2.5 | 0 | 0 | 5 | 5 | 5 | 5 | 5 |
|    | 10 | 0 | 0 | 5 | 4 | 5 | 5 | 5 |
| 17 | 2.5 | 0 | 0 | 5 | 5 | 5 | 5 | 5 |
|    | 10 | 0 | 0 | 5 | 5 | 5 | 5 | 4 |
| 18 | 2.5 | 0 | 0 | 5 | 5 | 5 | 5 | 5 |
|    | 10 | 0 | 0 | 5 | 5 | 3 | 5 | 4 |
| 20 | 2.5 | 0 | 0 | 5 | 5 | 5 | 5 | 5 |
|    | 10 | 0 | 0 | 5 | 5 | 5 | 5 | 4 |

TEST EXAMPLE 5

Plastic trays (35 cm×25 cm×15 cm) were filled with upland field soil, and the seeds of sugarbeet, cotton and soybeans and the seeds of green foxtail, johnsongrass, blackgrass, annual bluegrass and wild oat were sowed therein. A designed amount of the test compound formulated in a wettable powder according to Formulation Example 1 and diluted with water was sprayed to the soil surface over the top by means of a small hand sprayer at a spray volume of 5 liters per are. After 20 days, herbicidal activity and phytotoxicity were examined. The results are shown in Table 6.

TABLE 6

| Compound No. | Dosage (weight of active ingredient, g/are) | Phytotoxicity Soybean | Phytotoxicity Cotton | Phytotoxicity Sugarbeet | Herbicidal acitivity Green fox-tail | Johnson-grass | Black-grass | Annual blue-grass | Wild oat |
|---|---|---|---|---|---|---|---|---|---|
| 6 | 20 | 0 | 0 | 0 | 5 | 5 | 5 | 5 | 5 |
|   | 5 | 0 | 0 | 0 | 4 | 5 | 5 | 5 | 5 |
| 9 | 20 | 0 | 0 | 0 | 5 | 5 | 5 | 5 | 5 |
|   | 5 | 0 | 0 | 0 | 4 | 5 | 5 | 5 | 5 |
| 11 | 20 | 0 | 0 | 0 | 5 | 5 | 5 | 5 | 4 |
|    | 5 | 0 | 0 | 0 | 5 | 5 | 5 | 5 | 4 |
| 13 | 20 | 1 | 0 | 0 | 5 | 5 | 5 | 5 | 5 |
|    | 5 | 0 | 0 | 0 | 4 | 5 | 5 | 5 | 4 |
| 19 | 20 | 0 | 0 | 0 | 5 | 5 | 5 | 5 | 5 |
|    | 5 | 0 | 0 | 0 | 5 | 5 | 5 | 5 | 4 |

What is claimed is:

1. A compound of the formula:

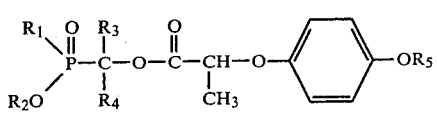

wherein $R_1$ is a $C_1$–$C_4$ alkyl group, a phenyl group or a $C_1$–$C_4$ alkoxy group, $R_2$ is a $C_1$–$C_4$ alkyl group, $R_3$ and $R_4$, which are the same or different, are each a hydrogen atom, a $C_1$–$C_4$ alkyl group or a phenyl group and $R_5$ is a 2,4-dichlorophenyl group, a 4-trifluoromethylphenyl group or a 5-trifluoromethylpyridin-2-yl group.

2. The compound according to claim 1, wherein $R_1$ is a $C_1$–$C_2$ alkyl group, a phenyl group or a $C_1$–$C_4$ alkoxy group, $R_2$ is a $C_1$–$C_4$ alkyl group, $R_3$ is a hydrogen atom, a $C_1$–$C_3$ alkyl group or a phenyl group, $R_4$ is a hydrogen atom or a methyl group and $R_5$ is a 2,4-dichlorophenyl group, a 4-trifluoromethylphenyl group or a 5-trifluoromethylpyridin-2-yl group.

3. The compound according to claim 1, which is O,O-dimethylphosphonomethyl α-4-(2′,4′-dichlorophenoxy)-phenoxypropionate.

4. The compound according to claim 1, which is O,O-diethylphosphonomethyl α-4-(4′-trifluoromethylphenoxy)phenoxypropionate.

5. The compound according to claim 1, which is α-(O,O-dimethylphosphono)ethyl α-4-(4′-trifluoromethylphenoxy)phenoxypropionate.

6. A herbicidal composition which comprises as an active ingredient a herbicidally effective amount of the compound of the formula:

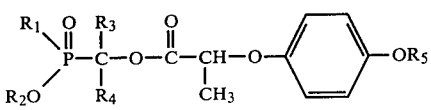

wherein $R_1$ is a $C_1$–$C_4$ alkyl group, a phenyl group or a $C_1$–$C_4$ alkoxy group, $R_2$ is a $C_1$–$C_4$ alkyl group, $R_3$ and $R_4$, which are the same or different, are each a hydrogen atom, a $C_1$–$C_4$ alkyl group or a phenyl group and $R_5$ is a 2,4-dichlorophenyl group, a 4-trifluoromethylphenyl group or a 5-trifluoromethylpyridin-2-yl group, and an inert carrier or diluent.

7. A method for controlling weeds which comprises applying as an active ingredient a herbicidally effective amount of the compound of the formula:

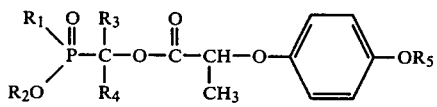

wherein $R_1$ is a $C_1$–$C_4$ alkyl group, a phenyl group or a $C_1$–$C_4$ alkoxy group, $R_2$ is a $C_1$–$C_4$ alkyl group, $R_3$ and $R_4$, which are the same or different, are each a hydrogen atom, a $C_1$–$C_4$ alkyl group or a phenyl group and $R_5$ is a 2,4-dichlorophenyl group, a 4-trifluoromethylphenyl group or a 5-trifluoromethylpyridin-2-yl group to the area where the weeds grow or will grow.

8. A compound of the formula:

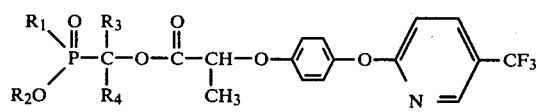

wherein $R_1$ is a $C_1$–$C_4$ alkyl group, a phenyl group or a $C_1$–$C_4$ alkoxy group, $R_2$ is a $C_1$–$C_4$ alkyl group, and $R_3$ and $R_4$, which are the same or different, are each a hydrogen atom, a $C_1$–$C_4$ alkyl group or a phenyl group.

9. The compound according to claim 8, which is O,O-diethylphosphonomethyl α-4-(5'-trifluoromethylpyridin-2-yloxy)phenoxypropionate.

10. The compound according to claim 8, wherein $R_1$ is a $C_1$–$C_4$ alkyl group.

11. The compound according to claim 8, wherein $R_1$ is a phenyl group.

12. The compound according to claim 8, wherein $R_1$ is a $C_1$–$C_4$ alkoxy group.

13. The compound according to claim 8, wherein $R_3$ and $R_4$ are each a hydrogen atom or a $C_1$–$C_4$ alkyl group.

14. The compound according to claim 8, wherein $R_3$ and $R_4$ are each a hydrogen atom or a phenyl group.

15. The compound according to claim 8, wherein $R_3$ and $R_4$ are each a $C_1$–$C_4$ alkyl group or a phenyl group.

16. A herbicidal composition which comprises as an active ingredient a herbicidally effective amount of the compound of claim 8, and an inert carrier or diluent.

17. A method for controlling weeds which comprises applying as an active ingredient a herbicidally effective amount of the compound of claim 8 to the area where the weeds grow or will grow.

18. The compound according to claim 8, wherein $R_3$ is a hydrogen atom, a $C_1$–$C_3$ alkyl group or a phenyl group and $R_4$ is a hydrogen atom or a methyl group.

19. The method of claim 17, wherein said compound is applied to a rice field.

20. The method of claim 17, wherein said compound is applied to a wheat field.

* * * * *